United States Patent [19]

Carr et al.

[11] Patent Number: 5,064,838

[45] Date of Patent: Nov. 12, 1991

[54] 1,4-DISUBSTITUTED-PIPERIDINYL COMPOUNDS AS PAIN RELIEVERS

[75] Inventors: Albert A. Carr, Cincinnati; Francis P. Miller, Loveland; Thaddeus R. Nieduzak; Stephen M. Sorensen, both of Cincinnati, all of Ohio

[73] Assignee: Merrell Dow Pharmaceuticals, Cincinnati, Ohio

[21] Appl. No.: 279,900

[22] Filed: Dec. 7, 1988

Related U.S. Application Data

[63] Continuation-in-part of Ser. No. 146,647, Jan. 21, 1988, abandoned.

[51] Int. Cl.$^5$ .................. A61K 31/445; C07D 211/20; C07D 261/20

[52] U.S. Cl. .................. 514/317; 546/248; 546/241

[58] Field of Search ............... 546/248, 241; 514/315, 514/317

[56] References Cited

U.S. PATENT DOCUMENTS 3,576,810  4/1971  Duncan, Jr. et al. ............. 514/315
3,959,291  5/1976  Cook ................................. 546/248

Primary Examiner—Mary C. Lee
Assistant Examiner—Robert C. Whittenbaugh
Attorney, Agent, or Firm—J. Michael Dixon

[57] ABSTRACT

The present invention relates to 1,4-disubstituted-piperidinyl compounds that have utility as analgesics and as muscle relaxants.

16 Claims, No Drawings

1,4-DISUBSTITUTED-PIPERIDINYL COMPOUNDS AS PAIN RELIEVERS

The instant application is a continuation-in-part of Ser. No. 146,647 which was filed on Jan. 21, 1988 now abandoned.

The present invention relates to 1,4-disubstituted-piperidinyl compounds which are useful as analgesics and muscle relaxants. Another aspect of the invention relates to methods for relieving pain. A further aspect of the present invention relates to methods for relieving muscle spasms.

A wide number of compounds are currently available which possess therapeutic activity as analgesics. Unfortunately, most of the more potent analgesics are narcotics. Narcotics are potentially addictive and therefore are prone to abuse by susceptible individuals.

There are also a large number of compounds available which are capable of relieving muscle spasms. Most of these compounds have undesirable side effects such as sedation and impairment of motor skills.

Thus, it would be a valuable contribution to the art to develop potent analgesics which are non-narcotic and therefore devoid of abuse potential.

It would also be a valuable contribution to the art to develop muscle relaxants which do not sedate the patient or impair his motor skills. In accordance with the present invention a new class of analgesics and muscle relaxants have been discovered. These compounds may be represented by the formulae:

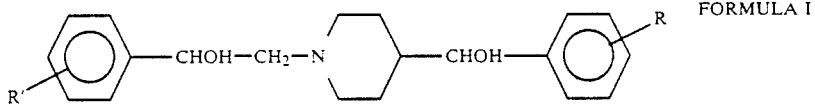

FORMULA I

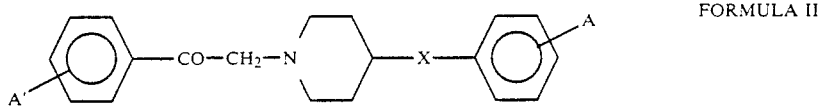

FORMULA II wherein:

a) in Formula I, each R and R' is independently selected from the group consisting of lower alkyl, lower alkoxy, hydrogen and halogen; and, b) in Formula II, X is represented by either a carbonyl group or a hydroxymethylene group; A' is at least one substituent selected from the group consisting of halogen, lower alkyl, and lower alkoxy; and, A is selected from the group consisting of halogen, hydrogen, lower alkyl, and lower alkoxy; with the proviso that when X is a carbonyl group, A' is not a halogen when A is a lower alkyl or lower alkoxy.

Additionally, it has been discovered that the following known compounds have utility as analgesics and as muscle relaxants:

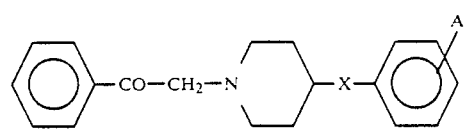

FORMULA III

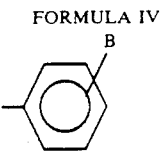

FORMULA IV wherein:

a) in Formula III, X is represented by a carbonyl group or a hydroxymethylene group; and A is selected from the group consisting of halogen, hydrogen, lower alkyl, and lower alkoxy; and, b) in Formula IV, each B and B' are independently selected from the group consisting of halogen, lower alkyl, lower alkoxy, and hydrogen; with the proviso that B' and B are not both halogens.

Thus, the compounds of the present invention which possess therapeutic utility as analgesics or muscle relaxants may be conveniently represented by the following generic formula:

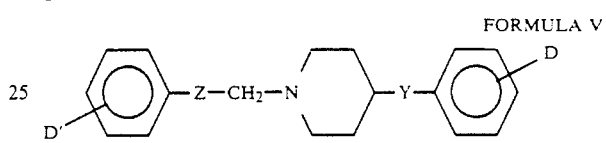

FORMULA V wherein:

Y is represented by a hydroxymethylene group or a carbonyl group; Z is represented by a hydroxymethylene group or a carbonyl group; each D and D' are independently selected from the group consisting of lower alkyl, lower alkoxy, halogen and hydrogen; with the following provisos: i) that when Y and Z are both represented by carbonyl groups, then D is not a lower alkyl or lower alkoxy when D' is a halogen; and, ii) that when Y is represented by a carbonyl group and Z is represented by a hydroxymethylene group, then D and D' are not both halogens.

As used in this application:

a) the term hydroxymethylene group refers to a structure corresponding to, —CHOH—;

b) the term carbonyl group refers to a structure corresponding to —CO—;

c) the term halogen refers to a fluorine, chlorine or bromine atom;

d) the term lower alkyl group refers to a branched or straight chain alkyl group containing from 1–4 carbon atoms, such as methyl, ethyl, n-propyl, isopropyl, n-butyl and isobutyl; and, e) the term lower alkoxy group refers to a straight or branched alkoxy group containing from 1–4 carbon atoms, such as methoxy, ethoxy, n-propoxy, isopropoxy, n-butoxy and isobutoxy.

The expression "pharmaceutically acceptable acid addition salts" is intended to apply to any non-toxic organic or inorganic acid addition salt of the base compounds represented by Formulae I-V. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methanesulfonic acid, p-toluenesulfonic acid and 2-hydroxyethane sulfonic acid.

Some of the compounds of Formulae I-V contain asymmetric centers. Any reference in this application to one of the compounds represented by Formulae I-V is meant to encompass either a specific optical isomer or a mixture of enantiomers or diasteriomers. The specific optical isomers can be separated and recovered by techniques known in the art such as chromatography on chiral stationary phases or resolution via chiral salt formation and subsequent separation by selective crystallization.

The specific optical isomers can also be resolved by the use of enantiospecific enzymes as is known in the art. For example in those compounds containing an alcohol, the alcohol is acylated with an acylating agent such as acetyl chloride, butyryl chloride, chloroacetyl chloride, or their equivalents. The compound containing the acylated alcohol is then contacted with a suitable enantiospecific enzyme thereby producing the desired stereoisomerically enriched alcohol via enzymatic hydrolysis. The desired alcohol can be separated from the complementary stereoisomerically enriched acylated alcohol by-product by chromatographic techniques as is known in the art. Examples of such enzymes include the fungal lipase Amano AP-12 ®, derived from *Asperqillus niqer* and the fungal lipase derived from *Candida cylindracea*. The acylation is typically conducted in an organic solvent such as DMF. The enzymatic hydrolysis is typically conducted in an aqueous buffer with or without an organic solvent such as hexane, heptane, chloroform, ethyl ether and dichloromethane. The quantity of enzyme can vary widely as known to those skilled in the art.

An alternative method of resolving those compounds of Formulae I-V which contain an alcohol is by enzymatic esterification. The racemic alcohol containing compound of Formulae I-V is contacted with a suitable enantiospecific enzyme, such as one of those described above, in the presence of an esterifying agent such butyric acid, palmytic acid, lauric acid, ethyl acetate, or dichloroethyl butyrate. The desired stereoisomerically enriched ester and the complementary stereoisomerically enriched alcohol by-product can be separated by conventional chromatographic techniques. After the desired ester is separated, it can be subjected to a basic hydrolysis to produce the desired compound. The enzymatic esterification is also typically conducted in an organic solvent such as one of those described above. Other enantiospecific enzymes are known in the art. Some of these may also be suitable for either of the resolution techniques discussed above as known to those skilled in the art.

Representative examples of suitable analgesics and muscle relaxants represented by Formulae I-V are those illustrated below:
a) (3,4-dimethoxyphenyl)[1-[2-(4-fluorophenyl)-2-hydroxyethyl]-4-piperidinyl]-methanone;
b) α-(4-fluorophenyl)-4-[(4-fluorophenyl)hydroxymethyl]-1-piperidineethanol;
c) 4-(hydroxyphenylmethyl)-α-phenyl-1-piperidineethanol;
d) α-(4-fluorophenyl)-4-(hydroxyphenylmethyl)-1-piperidineethanol;
e) 2-(4-benzoyl-1-piperidinyl)-1-phenyl-ethanone;
f) 2-[4-(4-fluorobenzoyl)-1-piperidinyl]-1-(4-fluorophenyl)-ethanone;
g) 1-(4-fluorophenyl)-2-[4-[(4-fluorophenyl)hydroxymethyl]-1-piperidinyl]-ethanone; and,
h) the pharmaceutically acceptable acid addition salts thereof.

Each of the phenyl rings contained within the compounds represented by Formulae I-V, may be substituted at up to three positions with the indicated chemical entities. These substitutions may be located at positions 2-6 of the phenyl ring. Each phenyl ring may be substituted with differing chemical entities or a single chemical entity. Thus, for example, in Formula V, D can represent up to 3 substituents which may be the same or differing chemical entities which are located at any of positions 2-6 on the indicated ring. It is also possible for the two phenyl rings contained within a compound to have differing substituents provided that the limitations of the provisos described above are followed.

If the phenyl rings are substituted, it is currently preferred for the substitutions to occur at either position 3 or 4 of the phenyl ring.

The more preferred compounds of the present invention are those of Formula I.

The most preferred compounds of the present invention are those selected from the group consisting of:
a) α-(4-fluorophenyl)-4-[(4-fluorophenyl)hydroxymethyl]-1-piperidineethanol;
b) 4-(hydroxyphenylmethyl)-α-phenyl-1-piperidineethanol; and,
c) α-(4-fluorophenyl)-4-(hydroxyphenylmethyl)-1-piperidineethanol.

The compounds of the present invention can be synthesized by techniques known in the art. A currently preferred and novel manner of preparing these compounds can be described by the following processes.

If the desired compound is a 1,4-disubstituted-piperidinyl diketone or a 1-(optionally substituted)-phenacyl-4-hydroxyarylmethyl-piperidine as described by Formulae II or III then the following synthesis can be utilized.

Starting materials are: a) a 4-substituted-piperidine as described by Formula VI, wherein X and A are as defined in Formulae II and III; and, b) an optionally-substituted-phenacyl halide as described by Formula VII, wherein A' is as described in Formula II or A' is absent as in Formula III and Y is a halogen, preferably chlorine.

FORMULA VI

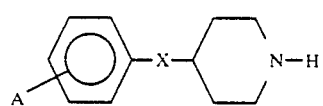

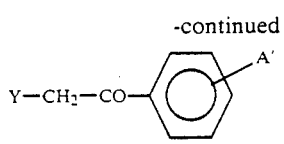

FORMULA VII

The 4-substituted-piperidine (compound of Formula VI) should correspond structurally to its counterpart in the desired 1,4-disubstituted-piperidinyl compound since all of the substituents on the 4-substituted-piperidine will be retained in the final product. Thus if X in the desired 1,4-disubstituted-piperidinyl compound is a carbonyl group, then the 4-substituted-piperidine of Formula VI utilized as a starting material should be substituted with a carbonyl group at the 4 position of the piperidinyl ring. Likewise, if X in the desired 1,4-disubstituted-piperidinyl compound is a hydroxymethylene group, then the 4-substituted-piperidine of Formula VI used as a starting material should be substituted with a hydroxymethylene group at the 4 position of the piperidinyl ring. If A in the desired 1,4-disubstituted-piperidinyl compound is a 4-fluorosubstituent, then the 4-substituted-piperidine should contain a fluorine at the 4-position of the indicated phenyl ring.

Likewise, the optionally-substituted-phenacyl halide (compound of Formula VII) should correspond structurally to its counterpart in the desired 1,4-disubstituted-piperidinyl compound since all of its substituents with the exception of the halogen atom represented by Y, will be retained in the final product. Thus, if A' is a 4-fluoro substituent, then the optionally-substituted-phenacyl halide should contain a fluorine at the 4-position of the indicated phenyl ring.

For example, if the desired 1,4-disubstituted-piperidinyl compound is 2-[4-(4-fluorobenzoyl)-1-piperidinyl]-1-(4-fluorophenyl)-ethanone, then the preferred starting materials are: a) 4-fluorophenyl-4-piperidinyl ketone; and, b) 2-chloro-4'-fluoroacetophenone.

It is currently preferred that approximately equimolar quantities of the 4-substituted-piperidine and the optionally-substituted-phenacyl halide be utilized in the synthesis. A slight excess of either of the reactants is not deleterious to the synthesis.

It is also preferred that the reaction be conducted in the presence of either an organic or inorganic base. Sodium bicarbonate is currently utilized. The base is preferably present in a molar excess relative to the 4-substituted-piperidine.

It is also preferred that the reaction be conducted in the presence of an alkali-iodo catalyst. Sodium iodide is currently utilized. The alkali-iodo catalyst is generally present in a quantity of from 0.1 to 1 mol percent based upon the quantity of 4-substituted-piperidine present in the reaction zone.

The 4-substituted-piperidine and the optionally-substituted-phenacyl halide are generally stirred together for a period of time ranging from 1 to 30 hours. It is preferred that the reaction be conducted at a temperature range of from 25° to 115° C. It is also preferred that the reaction be conducted in an organic solvent. Representative examples of suitable solvents include dichloromethane, methanol, tetrahydrofuran, toluene, chloroform, and the like.

The 1,4-disubstituted-piperidinyl compound produced above can be recovered from the reaction zone by techniques known in the art. One suitable technique is to extract the reaction zone with an organic solvent after water has been added to the reaction. The desired 1,4-disubstituted-piperidinyl compound will be found in the organic phase.

The 1,4-disubstituted-piperidinyl compound can then be purified by techniques known in the art. One such suitable technique is recrystallization from a suitable solvent system. Representative examples of suitable solvent systems include methanol/butanone and methanol/ethyl acetate if the desired compound is present as an acid addition salt. Ethyl acetate/hexane and chloroform/benzene are examples of suitable solvent systems if the desired compound is present as a free base. Other solvent systems known to those skilled in the art could also be utilized.

If the desired compound is a 1,4-disubstituted-piperidinyl diol as described by Formula I, then one method of preparing the compound is the following.

The starting material is a 1,4-disubstituted-piperidinyl diketone that can be described by the following formula VIII

FORMULA VIII

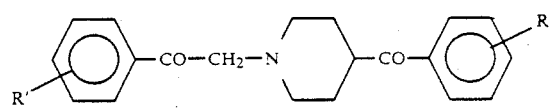

wherein R and R' are as defined in Formula I.

The desired 1,4-disubstituted-piperidinyl diol can then be obtained by reducing the piperidinyl diketone of Formula VIII with an appropriate reducing agent.

The 1,4-disubstituted-piperidinyl diketone (as described by Formula VIII) which is utilized in the reduction should correspond structurally to the desired 1,4-disubstituted-piperidinyl diol, since all of the diketones substituents (with the exception of the carbonyls) will be retained in the final product. Thus, if R' in the desired diol is a 4-fluoro-substituent, then the diketone utilized should be substituted with a fluorine atom at the 4-position of the indicated phenyl ring.

For example, α-(4-fluorophenyl)-4-[(4-fluorophenyl) hydroxymethyl]-1-piperidineethanol can be obtained by the reduction of 2-[4-(4-fluorobenzoyl)-1-piperidinyl]-1-(4-fluorophenyl)-ethanone.

The diketone starting material of Formula VIII can be obtained in the manner previously taught for preparing the diketone compounds of Formula II and III.

The reduction of the 1,4-disubstituted-piperidinyl diketone may be carried out with a variety of reducing agents as known to those skilled in the art. Lithium aluminum hydride and sodium borohydride are representative examples of suitable reducing agents. Sodium borohydride is currently preferred.

If sodium borohydride is utilized as the reducing agent, it is preferably present in the reaction zone in a molar excess relative to the the quantity of 1,4-disubstituted-piperidinyl diketone present and more preferably, is present in the molar ratio of from 2-4 moles of reducing agent for every mole of 1,4-disubstituted-piperidinyl diketone utilized.

It is currently preferred that the reduction be conducted at a temperature range of from 0° to 25° C. and for a period of time ranging from 1-24 hours. It is also preferred that the reaction be conducted in an organic solvent. Representative examples of suitable solvents include tetrahydrofuran and ether. Methanol is suitable for use with sodium borohydride.

After the reduction is completed, it is preferred that the reaction be quenched by the addition of water.

The 1,4-disubstituted-piperidinyl diol may then be recovered from the reaction zone by numerous techniques as known to those skilled in the art. One suitable technique is to extract the reaction zone with an organic solvent after the addition of water.

The 1,4-disubstituted-piperidinyl diol can then be purified by techniques known in the art. One such suitable technique is recrystallization from a suitable solvent system. Representative examples of suitable solvent systems include methanol/butanone and methanol/ethyl acetate if the desired compound is present as an acid addition salt. Ethyl acetate/hexane and chloroform/benzene are examples of suitable solvent systems if the desired compound is present as a free base. Other solvent systems known to those skilled in the art could also be utilized.

Alternatively, the 1,4-disubstituted-piperidinyl diol can be produced by reducing a 1-(optionally substituted)-phenacyl-4-hydroxyarylmethyl-piperidine as described in Formula II and III, that is structurally analogous to the desired piperidinyl diol. The reduction can be conducted in the same manner as that described above.

Likewise, the 1,4-disubstituted-piperidinyl diol can be produced by reducing an α-aryl-4-aroyl-piperidineethanol as described by Formula IV that is structurally analogous to the desired piperidinyl diol. The reduction should be conducted in a manner analogous to that described above.

Another alternative manner of preparing the 1,4-disubstituted-piperidinyl diols of Formula I can be described by the following procedure.

The starting materials can be described by the following formulae:

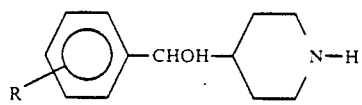

FORMULA IX

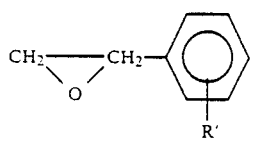

FORMULA X wherein R and R' are as defined in Formula I.

The 4-hydroxymethyl-substituted piperidine (compound of Formula IX) should be structurally analogous to its counterpart in the desired 1,4-disubstituted-piperidinyl diol since all of its substituents will be retained in the piperidinyl diol. Likewise, the optionally-substituted-styrene oxide (compound of Formula X) should be structurally analogous to its counterpart in the desired 1,4-disubstituted-piperidinyl diol since all of its substituents will be retained in the piperidinyl diol.

For example, 4-(hydroxyphenylmethyl)-α-phenyl-1-piperidineethanol can be prepared utilizing: i) 4-hydroxyphenylmethyl piperidine; and, ii) styrene oxide.

It is currently preferred that the optionally-substituted-styrene oxide and the 4-hydroxymethyl-substituted piperidine be present in the reaction zone in approximately equimolar quantities, although a slight excess of either reactant is not deleterious. They are generally reacted together for a period of time ranging from 1-24 hours. It is also preferred that they be reacted at a temperature range of from 25°-115° C.

The reaction is generally conducted in an organic solvent. Representative examples of suitable solvents include tetrahydrofuran, toluene, chloroform, dichloromethane and the like.

The desired 1,4-disubstituted-piperidinyl diol can be recovered from the reaction zone by techniques known in the art. The diols are currently recovered from the reaction by subjecting the diol-containing solvent to evaporation on a rotary evaporator.

The 1,4-disubstituted-piperidinyl diol can then be purified by techniques known in the art. One such suitable technique is recrystallization from a suitable solvent system. Representative examples of suitable solvent systems include methanol/butanone and methanol/ethyl acetate if the desired compound is present as an acid addition salt. Ethyl acetate/hexane and chloroform/benzene are examples of suitable solvent systems if the desired compound is present as a free base. Other solvent systems known to those skilled in the art could also be utilized.

The α-aryl-4-aroyl-piperidineethanol of Formula IV can be synthesized by techniques known in the art. The following novel synthetic method is preferred.

The starting materials are a 4-aroyl-substituted-piperidine as described by Formula XI and an optionally-substituted-styrene oxide as described by Formula XII

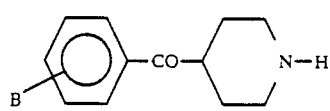

FORMULA XI

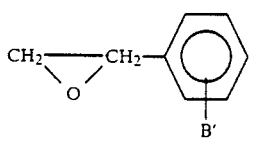

FORMULA XII wherein B and B' are as described in Formula IV.

The 4-aroyl-substitued piperidine should correspond structurally to its counterpart in the desired α-aryl-4-aroyl-piperidineethanol since all of its substituents will be retained in the final structure. The optionally-substituted-styrene oxide should also correspond structurally to its counterpart in the α-aryl-4-aroyl-piperidineethanol since all of its substituents will be retained in the final structure.

For example, if the desired α-aryl-4-aroyl-piperidineethanol is (3,4-dimethoxyphenyl)[1-[2-(4-fluorophenyl)-2hydroxyethyl]-4-piperidinyl]-methanone then the starting materials are: i) 3,4-dimethoxyphenyl-4-piperidinyl ketone; and, ii) 4-fluorostyrene oxide.

Preferably, approximately equimolar concentrations of the 4-aroyl-substituted-piperidine and styrene oxide are reacted together for a period of time ranging from 1-24 hours. A slight excess of either reactant is acceptable. It is also preferred that the reaction be conducted at a temperature of from 25°-115° C.

The reaction is generally conducted in an organic solvent. Representative examples of suitable solvents include tetrahydrofuran, toluene, chloroform, dichloromethane and the like.

The desired α-aryl-4-aroyl-piperidineethanol can be recovered from the reaction zone by numerous techniques as known in the art. One suitable technique is chromatography utilizing a silica gel adsorbent and an ethyl acetate eluent.

The desired α-aryl-4-aroyl-piperidineethanol can then be purified by techniques known in the art. One such suitable technique is recrystallization from a suitable solvent system. Representative examples of suitable solvent systems include methanol/butanone and methanol/ethyl acetate if the desired compound is present as an acid addition salt. Ethyl acetate/hexane and chloroform/benzene are examples of suitable solvent systems if the desired compound is present as a free base. Other solvent systems known to those skilled in the art could also be utilized.

As noted supra, the compounds described by Formula V may be utilized as analgesics. The compounds possess a level of potency sufficient to inhibit the sensation of the severe levels of pain that are commonly associated with conditions such as metastatic carcinoma, myocardial infarctions or traumatic injuries.

Despite this high level of potency, the compounds are non-narcotic. This means that they are devoid of the abuse potential that accompanies most analgesics.

One manner of demonstrating the analgesic utility of these compounds is to conduct the following test protocol. From 5 to 10 mice, should be administered from 0.1 to 200 mg/kg of the compound either subcutaneously or intragastrically. Thirty minutes after the administration of the test compound, the mice should be administered 0.4 ml of a 0.25% v/v solution of acetic acid intraperitoneally.

Five minutes after the administration of the acetic acid, the mice should be observed for signs of squirming and writhing which is indicative of pain.

A compound is considered to posses significant analgesic activity if the mice which are administered said compound do not exhibit signs of pain during the test (i.e., squirming and writhing).

One manner of demonstrating the non-narcotic properties of these compounds is the following test protocol.

Three mice should be administered up to 800 mg/kg of the desired compound subcutaneously. Thirty minutes later the mice should be placed upon a hot plate which has been heated to a temperature of 55° C.

A compound is considered to be non-narcotic if the mice jump within the first 20 seconds of when they are initially placed upon the hot plate.

One manner of demonstrating the utility of these compounds as muscle relaxants, is by their ability to antagonize the sustained contraction of the sacrococcygeus dorsalis muscle in mice, which the administration of morphine typically causes (Straub Tail Test). This may be demonstrated in the following manner.

From 5 to 10 mice should be administered from 0.1 to 200 mg/kg of the compound. Thirty minutes later the mice should be administered 60 mg/kg of morphine subcutaneously.

The mice should be observed for 30 minutes after the administration of the morphine in order to determine whether the test compound has blocked the ability of morphine to cause the sustained contraction of the sacrococcygeus dorsalis muscle in the mice. Contraction of this muscle causes the tails of the mice to be elevated at an angle of at least 90°. Thus if a compound is a muscle relaxant, the tails of the mice will not be elevated.

One manner of demonstrating that the compounds of the present invention do not impair motor skills or cause sedation is the following test protocol.

Mice are initially screened for use in the test by placing them on a horizontal rod which is rotating at 15 rpm. Those mice which fall off during a 120 second interval are excluded from further testing.

The mice satisfying the criterion described above are then administered up to 800 mg/kg either subcutaneously or intragastrically of the test compound.

Thirty minutes later the mice are placed back upon the rotating horizontal bar and observed for 90 seconds.

In order to determine if the compound is non-sedative and does not impair motor skills, it is necessary to interpret the results of this test in light of the $ED_{50}$ obtained in the Straub Tail test noted supra. A compound is considered to be non-sedative and to not impair motor skills, if the ratio between the dose at which approximately one-half of the mice fall off the rotating rod and the dose at which approximately one-half of the mice did not experience morphine induced contraction of the sacrococcygeus dorsalis muscle is about 2:1 or greater.

The compounds of the present invention may be administered by a variety of routes. They are effective if administered parenterally (i.e. subcutaneously, intravenously, intramuscularly, or intraperitoneally).

It is currently preferred that the compounds are administered parenterally. The quantity of the compound administered will vary depending on the patient, the mode of administration, and the severity of the condition that is being treated. Repetitive daily administration of the compounds may be desired and will vary with patient condition and mode of administration.

Although the dosage required will vary from patient to patient, it is generally preferred that the compounds of the present invention be administered within a dosage range of from 0.1-200 mg/kg of patient body weight/day whether being administered orally or parenterally. This dosage range is applicable whether the compounds are being utilized as an analgesic or as a muscle relaxant.

As used in this application, the term patient refers to a warm-blooded animal. Thus, the compounds are effective for the relief of pain and muscle spasms in birds, such as chickens and turkeys, or mammals, such as humans, primates, sheep, horses, cattle, pigs, dogs, cats, rats, and mice, etc.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formulae I-V can be tableted with conventional tablet bases such as lactose, sucrose, and cornstarch in combination with binders, such as acacia, cornstarch, or gelatin, disintegrating agents such as potato starch or algenic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art.

The following examples are presented in order to further illustrate the present invention. However, they should not be construed as limiting the scope of the invention in any manner.

EXAMPLE 1

The purpose of this example is to demonstrate one manner of preparing the 1,4-disubstituted-piperidinyl diketone, 2-[4-(4-fluorobenzoyl)-1-piperidinyl]-1-(4-fluorophenyl)-ethanone hydrochloride.

A mixture of 35.2 g (140 mmol) of 4-fluorophenyl-4-piperidinyl ketone hydrochloride, 27.6 g (160 mmol) of 2-chloro-4'-fluoroacetophenone, 30 g (300 mmol) of potassium hydrogen carbonate and 0.1 g of potassium iodide was added to 300 ml of toluene and 20 ml of water. This mixture was stirred at reflux for 24 hours.

The reaction mixture was then cooled and the organic layer was separated and saved for further purification. The aqueous layer was extracted with additional toluene and the organic layer was separated and saved for further purification.

The organic layers were combined and dried with anhydrous magnesium sulfate and then filtered. The resulting filtrate was treated with gaseous HCl while being cooled to approximately a temperature of 0° C.

The resulting precipitate was filtered off and recrystallized from a mixture of methanol and 2-butanone to give 2-[4-(4-fluorobenzoyl)-1-piperidinyl]-1-(4-fluorophenyl)-ethanone hydrochloride which had a melting point of 236°-237° C.

EXAMPLE 2

The purpose of this example is to demonstrate one manner of preparing the 1,4-disubstituted-piperidinyl diol, 2-(4-fluorophenyl)-4-[4-(4-fluorophenyl)hydroxymethyl]-1-piperidineethanol.

75.0 g (200 mmol) Of 2-[4-(4-fluorobenzoyl)-1-piperidinyl]-1-(4-fluorophenyl)-ethanone hydrochloride was prepared in the manner disclosed in Example 1. It was dissolved in 1500 ml of methanol. 37.5 g (1000 mmol) of sodium borohydride was added to this mixture in small portions over 1.5 hours. The mixture was then stirred overnight.

The reaction mixture was then diluted with 500 ml of water and stirred for 1.5 hours. Approximately 1500 ml of methanol was removed by rotary evaporation at reduced pressure. The resulting mixture was then extracted with chloroform.

The resulting organic layer was separated, dried with magnesium sulfate and then filtered. The resulting filtrate was then concentrated by rotary evaporation until an oil was obtained.

This oil was dissolved in 500 ml of isopropyl alcohol and cooled to a temperature of approximately 0° C. resulting in the formation of a precipitate.

The resulting precipitate was filtered off to obtain 2-(4-fluorophenyl)-4-[4-(4-fluorophenyl)hydroxymethyl]-1piperidineethanol which had a melting point of 103°-105° C.

EXAMPLE 3

The purpose of this example is to demonstrate one manner of preparing the 1,4-disubstituted-piperidinyl diol, α-(4-fluorophenyl)-4-(hydroxyphenylmethyl)-1-piperidineethanol.

First the 1,4-disubstituted-piperidinyl diketone starting material, 2-(4-benzoyl-1-piperidinyl)-1-(4-fluorophenyl)-ethanone hydrochloride was prepared in the following manner.

To a solution of 5.0 g (26.4 mmol) of phenyl-4-piperidinyl-ketone and 5.5 g (31.7 mmol) of 2-chloro-4'-fluoroacetophenone in 150 mol of methanol was added 10 g (119) mmol of sodium bicarbonate. This mixture was stirred for 24 hours at room temperature.

The solution was concentrated on a rotary evaporator and then diluted with water. This mixture was then extracted with ether. The resulting organic layer was separated and then washed with a solution of 10% aqueous hydrogen chloride. The resulting aqueous layer was basified with sodium carbonate and then extracted with chloroform.

The resulting organic layer was separated, dried with magnesium sulfate, filtered, and then concentrated on a rotary evaporator. The concentrate was treated with methanolic hydrogen chloride and concentrated on a rotary evaporator to yield a solid. The solid was purified by recrystallization from methanol/ethyl acetate.

6.0 g Of 2-(4-benzoyl-1-piperidinyl)-1-(4-fluorophenyl)-ethanone hydrochloride was obtained which had a melting point of 228°-233° C.

2.8 g Of the 2-(4-benzoyl-1-piperidinyl)-1-(4-fluorophenyl)-ethanone hydrochloride obtained above was dissolved in 100 ml of methanol and then 0.66 g of sodium borohydride was added. After stirring for 24 hours, the solution was diluted with ethyl acetate and washed with water.

The resulting organic layer was separated, dried with magnesium sulfate and filtered. The resulting filtrate was concentrated on a rotary evaporator thereby producing a solid. This solid was dissolved in ethyl acetate/hexane and the desired product was obtained by recrystallization.

1.3 g Of α-(4-fluorophenyl)-4-(hydroxyphenylmethyl)-1-piperidineethanol was obtained which had a melting point of 114°-116° C.

EXAMPLE 4

The purpose of this example is to demonstrate one manner of preparing the 1,4-disubstituted-piperidinyl diol, 4-(hydroxyphenylmethyl)-α-phenyl-1-piperidineethanol.

A mixture of 5.0 g (26.2 mmol) of 4-hydroxyphenylmethyl piperidine and 4.1 g (34.5 mmol) of styrene oxide was refluxed in 150 ml of toluene for 24 hours. This solution was then concentrated on a rotary evaporator and diluted with 10% aqueous hydrogen chloride.

This mixture was then extracted with ether. The resulting aqueous layer was separated, basified with sodium carbonate, and then extracted with ethyl acetate.

The resulting organic layer was dried with magnesium sulfate, stirred with activated charcoal, and filtered. The filtrate was concentrated on a rotary evaporator producing a yellow solid. This crude solid was admixed with cyclohexane and ethyl acetate, and the desired product was obtained by recrystallization from this medium. 5.5 g Of 4-(hydroxyphenylmethyl)-α-phenyl-1-piperidineethanol was obtained which had a melting point of 104° C.

EXAMPLE 5

The purpose of this example is to demonstrate a manner of preparing the α-aryl-4-aroyl-piperidineethanol, (3,4-dimethoxyphenyl)[1-[2-(4-fluorophenyl)-2-hydroxyethyl]-4piperidinyl]-methanone.

To a mixture of 1.0 g (3.5 mmol) of 3,4-dimethoxyphenyl4-piperidinyl ketone hydrochloride and 0.88 g (7.6 mmol) of 4-fluorostyrene oxide in 100 ml of toluene was added 0.44 g (3.8 mmol) of potassium carbonate.

This mixture was refluxed at a temperature of 115° C., for 48 hours. The resulting suspension was washed with water, dried with magnesium sulfate, filtered and then concentrated on a rotary evaporator. The resulting oil was subjected to chromatography on a silica gel column, utilizing 4% diethyl amine in ethylacetate as eluent.

The resulting eluent was concentrated by a rotary evaporator. The resulting solid was subjected to recrystallization in ethyl acetate and hexane producing 0.4 g of (3,4-dimethoxyphenyl)[1-[2-(4-fluorophenyl)-2-hydroxyethyl]4-piperidinyl]-methanone which had a melting point of 132°-136° C.

EXAMPLE 6

The purpose of this example is to demonstrate one manner of preparing the 1,4-disubstituted-piperidinyl diketone, 2-(4-benzoyl-1-piperidinyl)-1-phenylethanone hydrochloride.

A mixture of 25.4 g (130 mmol) of phenyl-4-piperidinyl ketone, 29.4 g (150 mmol) of α-bromoacetophenone and 20.9 g (150 mmol) of potassium carbonate in 300 ml of toluene was stirred at room temperature for 24 hours. This material was then refluxed for 24 hours.

The reaction mixture was cooled to 60° C., filtered, and then concentrated on a rotary evaporator to an oil.

The oil was dissolved in diethyl ether, treated with activated charcoal, and filtered. The filtrate was treated with a solution of HCl in ethyl acetate. The resulting precipitate was filtered and recrystallized from methanol-butanone to give 2-(4-benzoyl-1-piperidinyl)-1-phenyl-ethanone hydrochloride which had a melting point of 234.5°-237° C.

EXAMPLE 7

The purpose of this example is to demonstrate one method for preparing the 1-(substituted phenacyl)-4-hydroxyarylmethyl-piperidine, 1-(4-fluorophenyl)-2-[4-[(4-fluorophenyl)hydroxymethyl]-1-piperidinyl]-ethanone p-touenesulfonate.

To a solution of 10.0 g (47.8 mmol) of 4-[4-fluorophenylhydroxymethyl]-piperidine and 12.4 g (71.8 mmol) of 2-chloro-4'-fluoroacetophenone in 300 ml of dichloromethane was added 10 g (119 mmol) of sodium bicarbonate and a catalytic amount of sodium iodide.

After refluxing for 24 hours, the mixture was washed with a saturated solution of aqueous sodium bicarbonate, dried with magnesium sulfate, filtered and then concentrated on a rotary evaporator which produced a thick oil.

The thick oil was diluted with ether and then treated with p-touenesulfonic acid resulting in the formation of a precipitate.

The resulting precipitate was recovered by filtration and purified by recrystallization from ethyl acetate/methanol. 1-(4-Fluorophenyl)-2-[4-[(4-fluorophenyl)hydroxymethyl]-1-piperidinyl]-ethanone p-toulenesulfonate was obtained which had a melting point of 190°-193° C.

What is claimed is:

1. A compound of the formula:

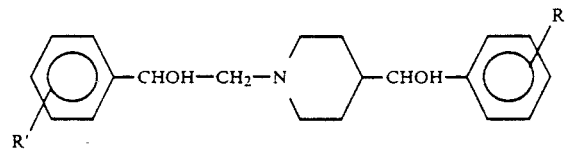

wherein each R and R' is independently selected from the group consisting of lower alkyl, lower alkoxy, hydrogen, and halogen, or a pharmaceutically acceptable salt thereof.

2. A compound according to claim 1, wherein said compound is α-(4-fluorophenyl)-4-[(4-fluorophenyl)hydroxymethyl]-1-piperidineethanol.

3. A compound according to claim 1, wherein said compound is 4-(hydroxyphenylmethyl)-α-phenyl-1-piperidine-ethanol.

4. A compound according to claim 1, wherein said compound is α-(4-fluorophenyl)-4-(hydroxyphenylmethyl)-1-piperidineethanol.

5. A method for relieving pain in a patient comprising administering to a patient in need thereof an effective amount of a compound according to claim 1.

6. A method for relieving muscle spasms comprising administering to a patient exhibiting said muscle spasm an effective amount of a compound according to claim 1.

7. A pharmaceutical composition comprising an effective amount of a compound according to claim 1 in admixture with a pharmaceutically acceptable carrier.

8. A composition according to claim 7, wherein said compound is α-(4-fluorophenyl-4-[(4-fluorophenyl)hydroxymethyl]-1-piperidineethanol.

9. A composition according to claim 7, wherein said compound is 4-(hydroxyphenylmethyl)-α-phenyl-1-piperidineethanol.

10. A composition according to claim 7 wherein said compound is α-(4-fluorophenyl)-4-(hydroxyphenylmethyl)-1-piperidineethanol.

11. A method according to claim 5, wherein said compound is α-(4-fluorophenyl)-4-[(4-fluorophenyl)hydroxymethyl]-1-piperidineethanol.

12. A method according to claim 5, wherein said compound is 4-(hydroxyphenylmethyl)-α-phenyl-1-piperidineethanol.

13. A method according to claim 5 wherein said compound is α-(4-fluorophenyl)-4-(hydroxyphenylmethyl)-1-piperidineethanol.

14. A method according to claim 6, wherein said compound is α-(4-fluorophenyl)-4-[(4-fluorophenyl)hydroxymethyl]-1-piperidineethanol.

15. A method according to claim 6, wherein said compound is 4-(hydroxyphenylmethyl)-α-phenyl-1-piperidineethanol.

16. A method according to claim 6 wherein said compound is α-(4-fluorophenyl)-4-(hydroxyphenylmethyl)-1-piperidineethanol.

* * * * *